(12) United States Patent
Hayakawa

(10) Patent No.: US 11,103,607 B2
(45) Date of Patent: Aug. 31, 2021

(54) METHOD AND APPARATUS FOR STERILIZING FILLING NOZZLE

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

(*) Notice: Subject to any disclaimer, the term of this patent is extended or adjusted under 35 U.S.C. 154(b) by 0 days.

(21) Appl. No.: 16/713,190

(22) Filed: Dec. 13, 2019

(65) Prior Publication Data

US 2020/0138992 A1 May 7, 2020

Related U.S. Application Data

(62) Division of application No. 15/511,691, filed as application No. PCT/JP2015/076718 on Sep. 18, 2015, now Pat. No. 10,556,028.

(30) Foreign Application Priority Data

Sep. 25, 2014 (JP) .............................. 2014-194746

(51) Int. Cl.
*A61L 2/18* (2006.01)
*B67C 7/00* (2006.01)
(Continued)

(52) U.S. Cl.
CPC .................. *A61L 2/18* (2013.01); *A61L 2/04* (2013.01); *B08B 3/02* (2013.01); *B08B 3/10* (2013.01);
(Continued)

(58) Field of Classification Search
CPC ..... A61L 2/04; A61L 2/16; A61L 2/18; A61L 2/24; A61L 2202/14; A61L 2202/17;
(Continued)

(56) References Cited

U.S. PATENT DOCUMENTS 4,414,036 A 11/1983 Anderson et al.
7,143,793 B2 12/2006 Vaughn, Jr.
(Continued)

FOREIGN PATENT DOCUMENTS

JP H05-026900 U 4/1993
JP 09-323794 A1 12/1997
(Continued)

OTHER PUBLICATIONS

International Search Report and Written Opinion (Application No. PCT/JP2015/076718) dated Dec. 22, 2015.
(Continued)

*Primary Examiner* — Timothy C Cleveland
(74) *Attorney, Agent, or Firm* — Burr & Brown, PLLC

(57) ABSTRACT

To simplify management of a sterilization process of a filling nozzle, a method for sterilizing a filling nozzle is provided, hot water or a liquid chemical agent is fed to drink supply piping that feeds a drink to a plurality of filling nozzles at the same time, the hot water or liquid chemical agent is discharged from all the filling nozzles, a flow rate of the hot water or liquid chemical agent is detected at all the filling nozzles, a representative temperature of the hot water or liquid chemical agent upstream or downstream of at least one filling nozzle is measured, and the sterilization process is ended when both the flow rate at each filling nozzle and the representative temperature reach respective target values.

6 Claims, 4 Drawing Sheets

(51) Int. Cl.
| | |
|---|---|
| *B08B 3/10* | (2006.01) |
| *B67C 3/00* | (2006.01) |
| *B08B 3/02* | (2006.01) |
| *B08B 9/032* | (2006.01) |
| *A61L 2/04* | (2006.01) |
| *B08B 9/023* | (2006.01) |

(52) U.S. Cl.
CPC ............ *B08B 9/023* (2013.01); *B08B 9/0321* (2013.01); *B08B 9/0325* (2013.01); *B67C 3/00* (2013.01); *B67C 3/005* (2013.01); *B67C 7/00* (2013.01); *A61L 2202/14* (2013.01); *A61L 2202/17* (2013.01); *B08B 2230/01* (2013.01)

(58) Field of Classification Search
CPC ........... B67C 3/00; B67C 3/001; B67C 3/005; B08B 3/02; B08B 3/10; B08B 9/023; B08B 9/0321; B08B 9/0325; B08B 2230/01
See application file for complete search history.

(56) References Cited

U.S. PATENT DOCUMENTS

| | | | |
|---|---|---|---|
| 7,491,371 | B2 | 2/2009 | Moller et al. |
| 7,857,910 | B2 | 12/2010 | Carhuff et al. |
| 2009/0320415 | A1 | 12/2009 | Senbon et al. |
| 2010/0170867 | A1 | 7/2010 | Hayakawa |
| 2013/0280127 | A1 | 10/2013 | Voth |
| 2013/0284309 | A1 | 10/2013 | Graff |
| 2015/0298178 | A1 | 10/2015 | Hayakawa |
| 2016/0046475 | A1 | 2/2016 | Hayakawa et al. |
| 2016/0121376 | A1 | 5/2016 | Hayakawa et al. |

FOREIGN PATENT DOCUMENTS

| | | |
|---|---|---|
| JP | H10-338296 A1 | 12/1998 |
| JP | 2000-153245 A1 | 6/2000 |
| JP | 2000-246192 A1 | 9/2000 |
| JP | 2004-001850 A1 | 1/2004 |
| JP | 2006-509690 A1 | 3/2006 |
| JP | 2007-022600 A1 | 2/2007 |
| JP | 2007-106464 A1 | 4/2007 |
| JP | 2007-215893 A1 | 8/2007 |
| JP | 2007-261639 A1 | 10/2007 |
| JP | 2004-331801 A1 | 12/2007 |
| JP | 2010-222053 A1 | 10/2010 |
| JP | 2013-224183 A1 | 10/2013 |
| JP | 2014-050479 A1 | 3/2014 |
| JP | 5574025 B1 | 8/2014 |
| JP | 5582213 B1 | 9/2014 |
| WO | 2014/077319 A1 | 5/2014 |
| WO | 2016/047604 A1 | 3/2016 |

OTHER PUBLICATIONS

Extended European Search Report (Application No. 15843260.9) dated May 4, 2018.
Japanese Office Action (Application No. 2017-114137) dated Sep. 4, 2018 (with English translation).
R.L. Earle, "Unit Operations in Food Processing Chapter 6: Heat-Transfer Applications," 1983.

METHOD AND APPARATUS FOR STERILIZING FILLING NOZZLE

CROSS REFERENCE TO RELATED APPLICATIONS

This application is a division of U.S. application Ser. No. 15/511,691, filed Mar. 16, 2017, which in turn is the National Stage entry of International Application No. PCT/JP2015/076718, filed Sep. 18, 2015, which designated the United States, the entireties of which are incorporated herein by reference.

FIELD OF THE INVENTION

The present invention relates to a method and an apparatus for sterilizing a filling nozzle of a filler that fills a container such as a PET bottle with a drink.

BACKGROUND OF THE INVENTION

When an aseptic filling apparatus fills a container such as a bottle with a drink, not only the drink itself has to be sterilized to be aseptic, but also drink supply piping of the aseptic filling apparatus including a surge tank, a liquid feeding pipe, a filler, and filling nozzles in the filler has to be cleaned and sterilized to be aseptic in advance.

With the drink supply piping of a conventional aseptic filling apparatus, CIP (Cleaning in Place) and SIP (Sterilizing in Place) are performed regularly or each time the kind of drink is changed (see Patent Documents 1, 2 and 3, for example).

CIP is performed by passing a cleaner containing water and an alkali agent such as caustic soda as an additive through a flow path from the pipe line of the drink filling path to the filing nozzles of the filler and then passing a cleaner containing water and an acid agent as an additive. CIP removes a residue of the previous drink in the drink filling path, for example (see Patent Documents 1, 2 and 3, for example).

SIP is a process to sterilize the interior of the drink supply piping before the drink filling operation is started, and is performed by passing a heated steam or hot water through the drink filling path cleaned by the CIP described above, for example. SIP sterilizes the interior of the drink filling path and makes it aseptic (see the paragraph [0003] in Patent Document 3, for example).

PRIOR ART DOCUMENT

Patent Document

Patent Document 1: Japanese Patent Laid-Open No. 2007-331801
Patent Document 2: Japanese Patent Laid-Open No. 2000-153245
Patent Document 3: Japanese Patent Laid-Open No. 2007-22600

SUMMARY OF THE INVENTION

Problems to be Solved by the Invention

Conventionally, when SIP as a sterilization process is performed on the drink supply piping of the aseptic filling apparatus, the drink supply piping is heated to 130° C. for 30 minutes. This sterilization condition is empirically considered to pose no problem about the sterilization effect. More specifically, heated steam or hot water is passed through the drink supply piping, the temperature of the drink supply piping is measured by temperature sensors at various positions where the temperature of the drink supply piping resists increasing, a timer is activated when the temperatures indicated by all the temperature sensors have reached 130° C., and the heating is ended when the temperature sensors have continued indicating a temperature higher than 130° C. for 30 minutes.

Typically, the drink supply piping branches into a large number of branch pipes via a manifold in the filler, and each branch pipe is connected to a filling nozzle at an end thereof. An experiment conducted by the inventor has shown that the large number of filling nozzles have different temperatures. Thus, to properly and quickly perform SIP, it is desirable to provide all the filling nozzles with a temperature sensor so that the F value can be measured at each filling nozzle. However, the temperature sensor is expensive, and there is a problem that the cost significantly increases if a temperature sensor is provided on each filling nozzle in a filler that has 100 or more filling nozzles, for example.

An object of the present invention is to provide a method and an apparatus for sterilizing a filling nozzle that can solve the problem described above.

Means for Solving the Problems

To solve the problem described above, the present invention is configured as described below.

In the description, to facilitate understanding of the present invention, reference numerals in the drawings are shown in parentheses. However, the present invention is not limited to the following description.

That is, the present invention according to a first aspect adopts a method for sterilizing a filling nozzle, wherein hot water or a liquid chemical agent is fed to drink supply piping (7) that feeds a drink to a plurality of filling nozzles (2a) at the same time, a flow rate of the hot water or liquid chemical agent is detected at all the filling nozzles (2a) while the hot water or liquid chemical agent is being discharged from all the filling nozzles (2a), a representative temperature of the hot water or liquid chemical agent upstream or downstream of at least one filling nozzle is measured, and a sterilization process is ended when both the flow rate at each filling nozzle and the representative temperature reach respective target values.

According to a second aspect of the present invention, in the method for sterilizing a filling nozzle according to the first aspect, an F value may be calculated based on the representative temperature, and it may be determined whether or not the F value has reached a target value.

According to a third aspect of the present invention, in the method for sterilizing a filling nozzle according to the first aspect, an alarm notifying a failure of the sterilization process may be issued if the flow rate at any of the filling nozzles (2a) is lower than a flow rate required for sterilization.

According to a fourth aspect of the present invention, in the method for sterilizing a filling nozzle according to the first aspect, an interior and an exterior of the filling nozzles (2a) may be sterilized at the same time by blasting hot water or a liquid chemical agent to the exterior of all the filling nozzles (2a) while the hot water or liquid or gaseous chemical agent is being discharged from all the filling nozzles (2a).

According to a fifth aspect of the present invention, in the method for sterilizing a filling nozzle according to the fourth aspect, the interior and the exterior of the filling nozzles may also be washed at the same time with the hot water or liquid chemical agent.

The present invention according to a sixth aspect adopts an apparatus for sterilizing a filling nozzle, wherein a flow rate sensor (10a) is provided on each of a plurality of filling nozzles (2a), hot water or a liquid chemical agent is fed to drink supply piping (7) that feeds a drink to the plurality of filling nozzles (2a) at the same time, a flow rate of the hot water or liquid chemical agent is detected at all the filling nozzles (2a) by the respective flow rate sensors (10a) while the hot water or liquid chemical agent is being discharged from all the filling nozzles (2a), a representative temperature of the hot water or liquid chemical agent upstream or downstream of at least one filling nozzle is measured by a temperature sensor, and a sterilization process is ended when both the flow rate at each filling nozzle and the representative temperature reach respective target values.

According to a seventh aspect of the present invention, in the apparatus for sterilizing a filling nozzle according to the sixth aspect, a drink metering sensor provided on each filling nozzle (2a) may be used as the flow rate sensor (10a).

According to an eighth aspect of the present invention, in the apparatus for sterilizing a filling nozzle according to the sixth aspect, an F value may be calculated based on the representative temperature, and it may be determined whether or not the F value has reached a target value.

According to a ninth aspect of the present invention, in the apparatus for sterilizing a filling nozzle according to the sixth or seventh aspect, an alarm notifying a failure of the sterilization process may be issued if the flow rate at any of the filling nozzles (2a) is lower than a flow rate required for sterilization.

According to a tenth aspect of the present invention, in the apparatus for sterilizing a filling nozzle according to the sixth aspect, all the filling nozzles (2a) may be capable of integrally rotating, and during the rotation, an interior and an exterior of the filling nozzles (2a) may be sterilized at the same time by blasting hot water or a liquid or gaseous chemical agent to the exterior of all the filling nozzles (2a) while the hot water or liquid chemical agent is being discharged from all the filling nozzles (2a).

According to a eleventh aspect of the present invention, in the apparatus for sterilizing a filling nozzle according to the tenth aspect, the interior and the exterior of the filling nozzles may also be washed at the same time with the hot water or liquid chemical agent.

Effects of the Invention

According to a method for sterilizing a filling nozzle according to the present invention, hot water or a liquid chemical agent is fed to drink supply piping (7) that feeds a drink to a plurality of filling nozzles (2a) at the same time, a flow rate of the hot water or liquid chemical agent is detected at all the filling nozzles (2a) while the hot water or liquid chemical agent is being discharged from all the filling nozzles (2a), a representative temperature of the hot water or liquid chemical agent upstream or downstream of at least one filling nozzle is measured, and a sterilization process is ended when both the flow rate at each filling nozzle and the representative temperature reach respective target values. Since the representative temperature is measured, it can be confirmed whether or not the interior of the filling nozzles has been properly sterilized. Since the flow rate of the hot water or liquid chemical agent in each filling nozzle is measured, it can be confirmed whether or not the valves of all the filling nozzles have been normally opened, the hot water or liquid chemical agent has smoothly flowed in all the filling nozzles, and the interior of the filling nozzles has been properly sterilized. In addition, since the need of providing the expensive temperature sensor on each filling nozzle is eliminated, and only the representative temperature is measured, SIP of the filler (2) can be managed at relatively low cost.

In addition, the drink metering sensor provided on each filling nozzle (2a) may be used as the flow rate sensor (10a). In that case, the filler (2) can be manufactured at low cost, and the structural complexity of the filler (2) can be reduced.

DETAILED DESCRIPTION OF THE INVENTION

In the following, embodiments of the present invention will be described with reference to the drawings.

First Embodiment

Figure 1:
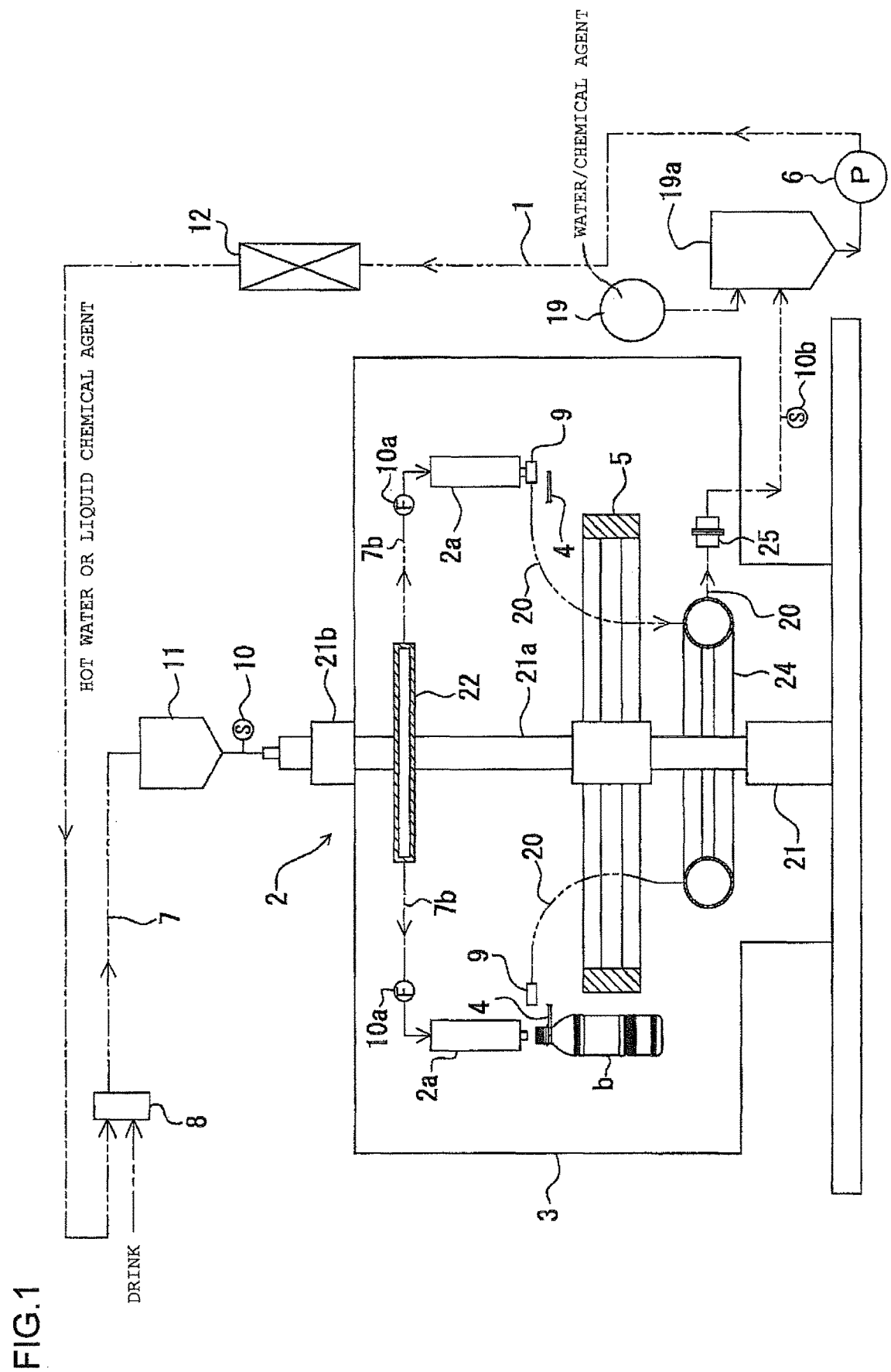
FIG. 1 is a schematic diagram showing a filler provided with an apparatus for sterilizing a filling nozzle according to the present invention, the right half of FIG. 1 showing the filler being subjected to SIP, and the left half of FIG. 1 showing the filler filling a bottle with a drink.

As shown in FIG. 1, an aseptic filling apparatus includes a filler 2, and the filler 2 includes a large number of filling nozzles 2a arranged at predetermined angular intervals in a predetermined horizontal plane.

The aseptic filling apparatus has a drink preparation unit (not shown), and the preparation unit feeds a drink to the filler 2 via a manifold valve 8.

The preparation unit, which produces a drink such as tea or fruit juice by mixing ingredients in desired proportions, is well-known and thus will not be described in detail herein.

The preparation unit and the filling nozzles 2a in the filler 2 are coupled to each other by drink supply piping 7. Along the flow path of the drink supply piping 7 from the preparation unit to the filler 2, the manifold valve 8 and a head tank 11 are disposed in this order from upstream to downstream of the flow of the drink. The drink supplied to the filler 2 through the drink supply piping 7 is metered and supplied into a bottle b, which is a container, through each filling nozzle 2a.

The aseptic filling apparatus includes a bottle conveying path that conveys the bottle b to the filler 2 and conveys the bottle b filled with the drink by the filler 2 to a capper (not shown). The bottle conveying path is typically formed by a series of a large number of wheels and grippers 4 disposed around the respective wheels, for example.

The filler 2 is a filling machine that fills a large number of bottles b with a drink at high rate and includes a wheel 5, which forms a part of the conveying path for the bottles b, as shown in FIG. 1. The wheel 5 is attached to a part forming a pivot 21a of a spindle 21 that stands vertically from a floor surface of the aseptic filling apparatus. The grippers 4 that grasp neck portions of the bottles b are arranged at regular intervals around the wheel 5. The grippers 4 can rotate in one direction integrally with the wheel 5. In addition, the large number of filling nozzle 2a are arranged at the same intervals as the grippers 4 around the wheel 5.

An upper part of the spindle 21, which is inhibited from rotating, is fixed to a casing of the filler 2. The pivot 21a is provided with a rotary joint 21b at an upper part thereof corresponding to the position where the spindle 21 is fixed. An upper manifold 22 is arranged on the pivot 21a at a position below the rotary joint 21b. A part of the spindle 21 from the top to the upper manifold 22 is hollow, and the drink supply piping 7 is introduced into the hollow part at the top of the spindle 21. Branch pipes 7b of the drink supply piping 7 extend from the upper manifold 22 to the filling nozzles 2a.

In operation of the filler 2, the wheel 5 rotates at high speed, the bottles b grasped by the grippers 4 are conveyed at high speed on the conveying path in synchronization with the rotation of the wheel 5, and a predetermined amount of the drink is supplied successively to each bottle b when the bottle b is located directly below the nozzle mouth at the lower end of the filling nozzle 2a. Each filling nozzle 2a is provided with a drink metering sensor (not shown), and thus, the drink is metered by the drink metering sensor and supplied into each bottle b.

The filler 2 is housed in an aseptic chamber 3 in its entirety as shown in FIG. 1 so that a sterilized bottle b can be filled with a sterilized drink by preventing a foreign matter such as microorganisms from entering the bottle b. Although not shown, the aseptic chamber 3 has an inlet port and an outlet port for the bottles b at an upstream part and a downstream part of the conveying path for the bottles b, respectively.

Before supplying the drink to the drink supply piping 7, hot water or a liquid chemical agent is supplied to the interior of the filler including the interior of the filling nozzles to perform SIP as a sterilization process.

As the chemical agent, hydrogen peroxide, peracetic acid, acetic acid, ozone water, sodium hypochlorite, sodium hydroxide, potassium hydroxide, acid water, chlorine dioxide or a mixture thereof can be used. Any other liquid that can inactivate microorganisms can be used.

To properly achieve SIP, the filler is provided with a sterilizing apparatus described below.

Specifically, a SIP cup 9 is arranged at the nozzle mouth of each filling nozzle 2a of the filler 2 in such a manner that the SIP cup 9 can be connected to and separated from the nozzle mouth. A drain pipe 20 formed by a flexible pipe is connected to each cup 9. When SIP is performed, the cup 9 is placed over the nozzle mouth at the tip end of the filling nozzle 2a of the filler 2 by an actuator (not shown), and a leading end of the drain pipe 20 is connected to the opening of the filling nozzle 2a.

At a predetermined position along the drink supply piping 7 between the head tank 11 and the interior of the filler 2, a temperature sensor 10 is disposed to detect the temperature of the hot water or liquid chemical agent supplied to perform SIP as a sterilization process in the drink supply piping 7.

Information about the temperature measured by the temperature sensor 10 is transmitted to a controller (not shown), so that a representative temperature of the hot water or liquid chemical agent upstream of at least one filling nozzle 2a can be monitored. This monitoring is achieved based on an F value calculated from the representative temperature or the like as described later. A common temperature monitoring is also possible, although the monitoring based on the F value is preferred from the viewpoint of energy savings.

Each of the plurality of filling nozzles 2a of the filler 2 is provided with a flow rate sensor 10a. When the hot water or liquid chemical agent is fed to the drink supply piping 7, the hot water or liquid chemical agent is discharged from all the filling nozzles 2a. In this process, the flow rate of the hot water or liquid chemical agent is detected at all the filling nozzles 2a by the respective flow rate sensors 10a, and the flow rate sensors 10a each transmit a flow rate signal to the controller. The flow rate signals are also used in monitoring of SIP as described later.

The drink metering sensor provided on each filling nozzle 2a may be used instead of the flow rate sensor 10a. Each filling nozzle 2a is provided with the drink metering sensor that allows the drink supplied to the drink supply piping 7 to be supplied in a predetermined amount into the container after SIP. When the drink metering sensor is used instead of the flow rate sensor 10a, the flow rate of the hot water or liquid chemical agent flowing through each filling nozzle 2a can be measured by the drink metering sensor, and the measurement value can be transmitted to the controller.

Each cup 9 described above is coupled to a lower manifold 24 by the drain pipe 20. The lower manifold 24 is attached to the pivot 21a of the filler 2 and can rotate integrally with the wheel 5, the filling nozzles 2a and the like.

The drain pipe 20 is provided with a disconnectable coupling 25 at a part where the drain pipe 20 extending from the lower manifold 24 exits to the outside of the aseptic chamber 3. When SIP described above is performed, the coupling 25 is connected. In this state, the wheel 5, the filling nozzles 2a and the like are inhibited from rotating. When SIP is completed, and the coupling 25 is disconnected, the wheel 5, the filling nozzles 2a and the like are allowed to rotate.

The drain pipe 20 is also provided with a temperature sensor 10b at a part outside the aseptic chamber 3. Information about the temperature measured by the temperature sensor 10b is also transmitted to the controller, so that a representative temperature of the hot water or liquid chemical agent downstream of at least one filling nozzle 2a can be monitored. This monitoring is achieved based on the F value calculated from the representative temperature or the like as described later. Instead of the monitoring based on calculation of the F value, a common temperature monitoring is also possible.

From the coupling 25 on the opposite side to the drain pipe 20, a return pipe 1 extends to the manifold valve 8. The return pipe 1 is provided with a reservoir tank 19a of the hot water or chemical agent, a pump 6, a heater 12 and the like at predetermined positions. The water, hot water or chemical agent is supplied to the reservoir tank 19a from a supply source 19 thereof. The pump 6 and the heater 12 may be provided on another pipe line such as the drink supply piping 7, instead of being provided on the return pipe 1.

The hot water or liquid chemical agent is heated to a predetermined temperature by the heater 12 and is fed under pressure by the pump 6 to circulate in an annular flow path formed by the drink supply piping 7, the drain pipe 20 and the return pipe 1. In this process, the hot water or liquid chemical agent sterilizes the interior of the filling nozzles 2a and the interior of the filler 2.

The controller uses temperature information from the various kinds of temperature sensors 10 and 10b to calculate the F value. In addition, the controller compares a representative temperature with a reference temperature and provides a predetermined output. In addition, the controller provides a predetermined output based on flow rate information from the flow rate sensor 10a. Based on the various kinds of outputs of the controller, the manifold valve 8 provided on the drink supply piping 7, the actuator (not shown), various kinds of switch valves, various kinds of pumps or the like are controlled.

Next, a method for sterilizing the filling nozzles 2a or filler 2 described above will be described.

(1) When an operation button on a panel of the controller (not shown) is manipulated, the manifold valve 8 disconnects the drink supply path, the cup 9 is placed on the nozzle mouth of the filling nozzle 2a to connect the drain pipe 20 to the filling nozzle 2a, as shown in the right half of FIG. 1. In addition, the return pipe 1 is connected to the coupling 25.

(2) The pump 6 is then activated to introduce the hot water or liquid chemical agent into the annular flow path formed by the drink supply piping 7, the drain pipe 20 and the return pipe 1.

(3) While the hot water or liquid chemical agent is flowing in the annular flow path, temperature information is transmitted from the temperature sensors 10 and 10b disposed at different positions to the controller at regular time intervals.

Figure 4:
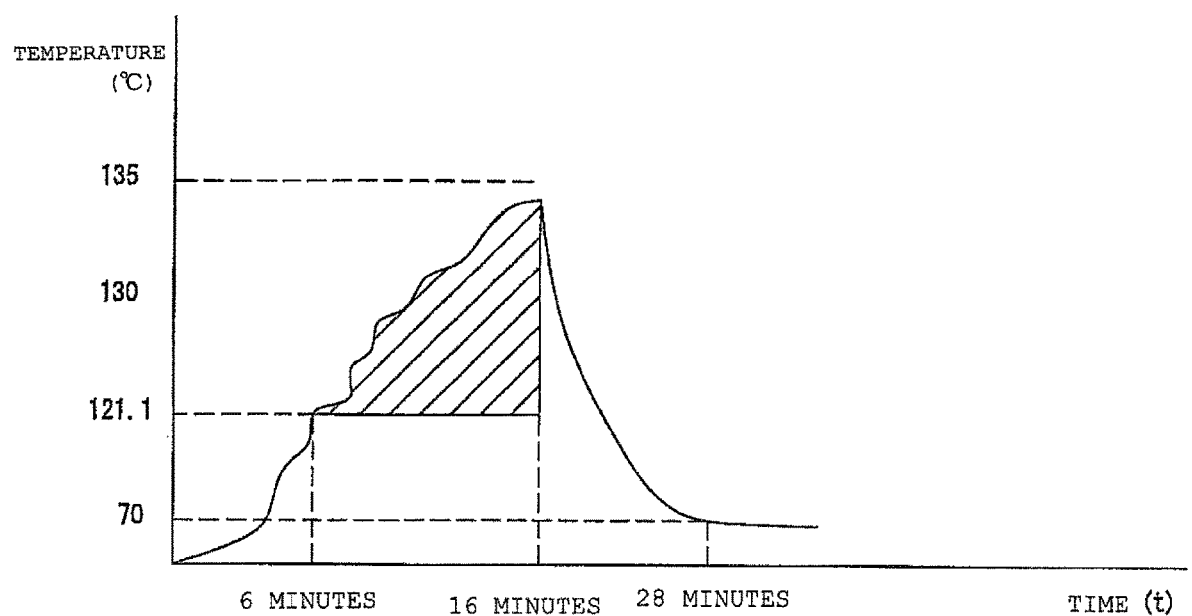
FIG. 4 is a graph for illustrating a time-temperature relationship of a method of heating the filler.

As shown in FIG. 4, when the temperatures of the drain pipe 20 and other parts heated by the hot water or liquid chemical agent reach 121.1° C., the controller starts calculating the F value at each position according to the following formula.

$$F = \int_{t_0}^{t_1} 10^{(T-121.1)/10} dt \quad \text{[formula 1]}$$

In this formula, T denotes an arbitrary sterilization temperature (° C.), and $10^{(T-121.1)/10}$ represents the fatality rate at an arbitrary temperature T and corresponds to the heating duration (in minutes) at 121.1° C. In this term, 121.1 is a reference temperature (° C.), and 10 is a Z value (° C.).

The controller determines whether or not the smallest one of the calculated F values has reached a target value.

With regard to the temperature sensor 10 at a position, the target value of the F value corresponds to the area of the hatched region in FIG. 4.

According to this embodiment, it is assumed that the drink that is the product liquid with which the bottle b is filled has a pH of 4.6 or higher, a reference temperature Tr is 121.1° C., and the Z value is 10° C.

In the formula for calculating the F value described above, the reference temperature Tr and the Z value can be changed according to the kind of the drink that is the product liquid.

For example, if the pH of the product liquid is equal to or higher than 4 and lower than 4.6, the reference temperature Tr can be 85° C., and the Z value can be 7.8° C. If the pH of the product liquid is lower than 4, the reference temperature Tr can be 60° C., and the Z value can be 5° C.

The values to be substituted into the formula described above can be changed as appropriate according to the ease of development of microorganisms, the temperature during distribution or the like of the product liquid, such as a hot-packed product such as green tea, mineral water or a chilled drink.

(4) Flow rate information is transmitted from the flow rate sensor 10a attached to each filling nozzle 2a to the controller at regular time intervals.

A relationship between the flow rate of the hot water or liquid chemical agent passing through each filling nozzle 2a and the effect of sterilization of the filling nozzle 2a can be determined by experiment in advance. Based on the result of the experiment, the controller determines whether or not the smallest one of the flow rates of all the filling nozzles 2a has reached the target value. In general, whether the hot water or chemical agent is used, a sufficient sterilization effect can be achieved if the flow rate at each filling nozzle is 1.5 m/s or higher, although some experiment result may show that a lower flow rate poses no problem.

(5) The controller monitors the flow rate of the hot water or liquid chemical agent at each filling nozzle 10a based on the flow rate information from the relevant flow rate sensor 2a, monitors the representative temperatures of the hot water or liquid chemical agent upstream and downstream of at least one filling nozzle 10a based on the temperature information from the temperature sensors 10 and 10b, and outputs a signal to complete the sterilization process when the flow rate and the representative temperatures reach the respective target values.

That is, when the minimum value of the F values based on the temperature information from the temperature sensors 10 and 10b reaches the target value, and the minimum value of the flow rates detected by the flow rate sensors 10a reaches the target value, the controller issues a signal to complete the sterilization process in the filler 2.

In response to the signal, the pump 6 is stopped, and the cups 9 are removed from the nozzle mouths of the filling nozzles 2a by the actuator (not shown). The coupling 25 is also disconnected.

When the flow rate at any of the filling nozzles 2a is lower than a flow rate required for sterilization, the controller may issue an alarm notifying a failure of the sterilization process. Based on the alarm, an operator can perform an adjustment to increase the flow rate of the hot water or the like at the relevant filling nozzle 2a.

(6) When sterilization with the liquid chemical agent is to be ended, the pump 6 or the like is stopped after the interior of the filler 2 or the like is rinsed with washing water. Aseptic air is then supplied into the head tank 11 to keep the whole of the drink supply piping 7 at positive pressure.

(7) After that, the process of filling the bottles b with the drink is started, and the drink prepared in the preparation unit is fed from the drink supply piping 7 into the filler 2 and supplied into the bottle b as a container through the filling nozzle 2a of the filler 2.

The bottle b filled with the drink is fed out of the filler 2 and then capped and sealed by the capper (not shown).

Second Embodiment

Figure 2:
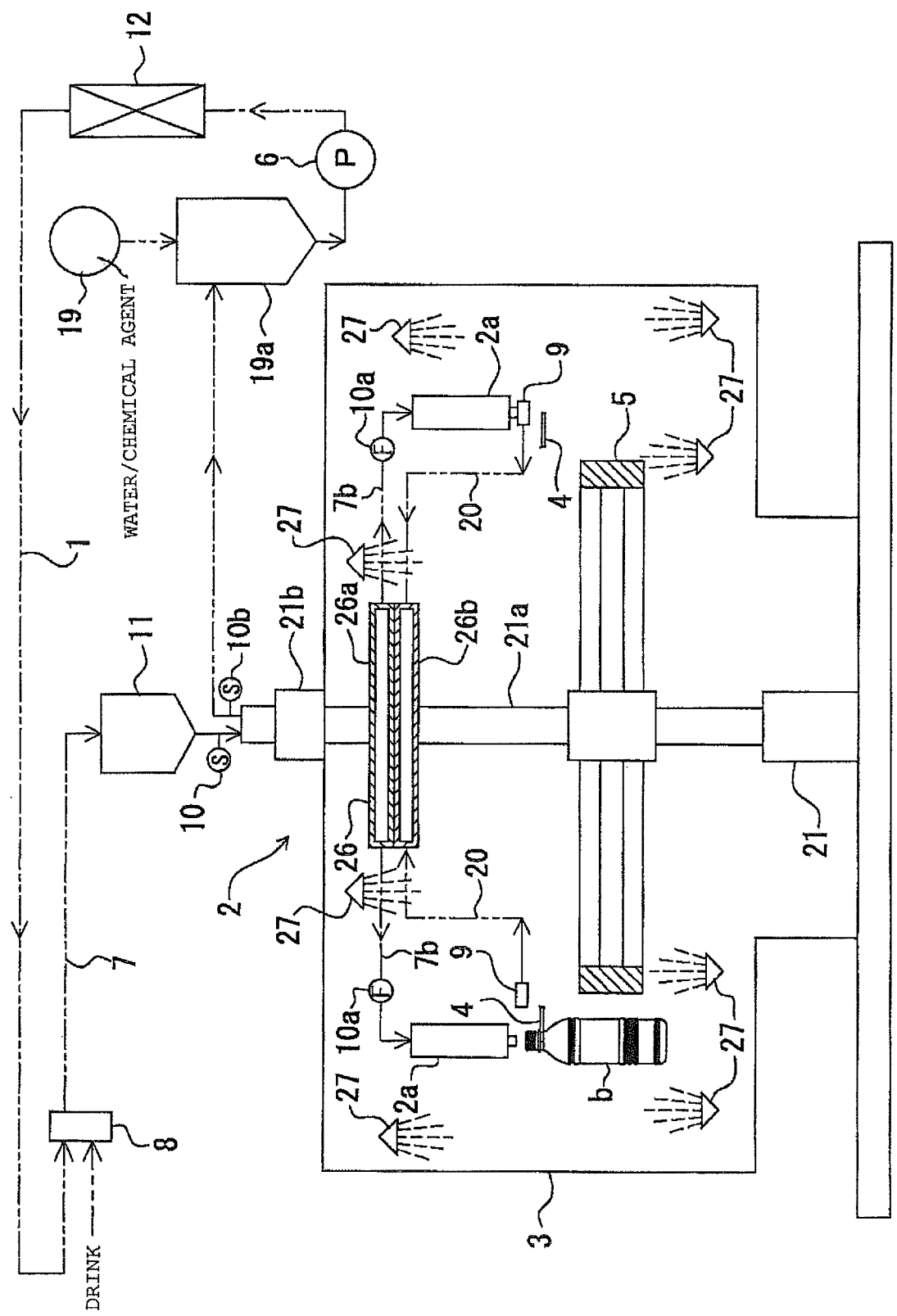
FIG. 2 is a schematic diagram showing another embodiment of the present invention.

As shown in FIG. 2, according to a second embodiment, a two-stage rotary joint 21c is provided on the pivot 21a.

In addition, a two-stage manifold 26 is provided on the pivot 21a at a position below the rotary joint 21b.

A part of the spindle 21 from the top to an upper-stage manifold 26a is hollow, and the drink supply piping 7 is coupled to the top of the spindle 21. Branch pipes 7b of the drink supply piping 7 radially extend from the upper-stage manifold 26a to the filling nozzles 2a.

In operation of the filler 2, the wheel 5 rotates at high speed, the bottles b grasped by the grippers 4 are conveyed at high speed on the conveying path in synchronization with the rotation of the wheel 5, and a predetermined amount of the drink is supplied successively to each bottle b when the bottle b is located directly below the nozzle mouth at the lower end of the filling nozzle 2a.

Before supplying the drink to the drink supply piping 7, hot water or a liquid chemical agent is supplied to the interior of the filler 2 including the interior of the filling nozzles 2a to perform SIP as a sterilization process.

To properly achieve SIP, the filler 2 is provided with a sterilizing apparatus described below.

Specifically, the SIP cup 9 is arranged at the nozzle mouth of each filling nozzle 2a of the filler 2 in such a manner that the SIP cup 9 can be connected to and separated from the nozzle mouth. The drain pipe 20 formed by a flexible pipe is connected to each cup 9. When SIP is performed, the cup 9 is placed over the nozzle mouth at the tip end of the filling nozzle 2a of the filler 2 by the actuator (not shown), and a leading end of the drain pipe 20 can be connected to the opening of the filling nozzle 2a.

At a position along the drink supply piping 7 between the head tank 11 and the interior of the filler 2, the temperature sensor 10 is disposed to detect the temperature of the hot water or liquid chemical agent supplied to perform SIP as a sterilization process in the drink supply piping 7.

Since the pivot 21a is provided with the rotary joint 21b as described above, the filling nozzles 2a and the like can rotate with the pivot 21a while the hot water or liquid chemical agent is flowing in the annular flow path. Thus, as shown in FIG. 2, when SIP is performed on the filling nozzles 2a, at the same time, COP (cleaning out of place), which is a cleaning process, or SOP (sterilizing out of place), which is a sterilization process, can be efficiently performed on the interior of the chamber 3 including the exterior of the filler 2 and the like by injecting water, a cleaning agent, hot water, a liquid or gaseous sterilizer or the like from spray nozzles 27 arranged at various positions in the chamber 3. The sterilizer preferably contains liquid or gaseous hydrogen peroxide. However, the sterilizer may contain other constituents, such as acetic acid, peracetic acid, ozone, chlorine dioxide, sodium hypochlorite, sodium hydroxide or potassium hydroxide.

Information about the temperature measured by the temperature sensor 10 is transmitted to the controller, so that a representative temperature of the hot water or liquid chemical agent upstream of at least one filling nozzle 2a can be monitored. Instead of the monitoring based on calculation of the F value, a common temperature monitoring is also possible.

Each of the plurality of filling nozzles 2a of the filler 2 is provided with the flow rate sensor 10a. When the hot water or liquid chemical agent is fed to the drink supply piping 7, the hot water or liquid chemical agent is discharged from all the filling nozzles 2a. In this process, the flow rate of the hot water or liquid chemical agent is detected at all the filling nozzles 2a by the respective flow rate sensors 10a, and the flow rate sensors 10a each transmit a flow rate signal to the controller. The flow rate signals are also used in monitoring of SIP as described later.

The drink metering sensor (not shown) provided on each filling nozzle 2a may be used instead of the flow rate sensor 10a. Each filling nozzle 2a is provided with the drink metering sensor that allows the drink supplied to the drink supply piping 7 to be supplied in a predetermined amount into the bottle b that is the container after SIP. When the drink metering sensor is used instead of the flow rate sensor 10a, the flow rate of the hot water or liquid chemical agent flowing through each filling nozzle 2a can be measured by the drink metering sensor, and the measurement value can be transmitted to the controller.

Each cup 9 described above is coupled to a lower-stage manifold 26b by the drain pipe 20. The second manifold 26b is also attached to the pivot 21a of the filler 2 and can rotate integrally with the wheel 5, the filling nozzles 2a and the like.

The spindle 21 has another hollow part between the top thereof and the lower-stage manifold 26b, and the return pipe 1 is coupled to the hollow part at the top of the spindle 21.

The return pipe 1 is provided with the temperature sensor 10b at a position outside the spindle 21. Information about the temperature measured by the temperature sensor 10b is transmitted to the controller, so that a representative temperature of the hot water or liquid chemical agent downstream of at least one filling nozzle 2a can be monitored. This monitoring is achieved based on the F value calculated from the representative temperature or the like as described later. Instead of the monitoring based on calculation of the F value, a common temperature monitoring is also possible.

The return pipe 1 extends to the manifold valve 8. The return pipe 1 is provided with the reservoir tank 19a of the water or chemical agent, the pump 6, the heater 12 and the like at predetermined positions. The water or chemical agent is supplied to the reservoir tank 19a from the supply source 19 thereof. The pump 6 and the heater 12 may be provided on another pipe line such as the drink supply piping 7, instead of being provided on the return pipe 1.

The water or liquid chemical agent is heated by the heater 12 and is fed under pressure by the pump 6 to circulate in the annular flow path formed by the drink supply piping 7, the upper-stage manifold 26a, the branch pipes 7b, the filling nozzles 2a, the drain pipe 20, the lower-stage manifold 26b and the return pipe 1 and heat the annular flow path. In this process, the hot water or liquid chemical agent sterilizes the interior of the filling nozzles 2a and the interior of the filler 2.

The controller calculates the F value based on the temperature information from the various kinds of temperature sensors 10 and 10b. In addition, the controller compares the representative temperature with the reference temperature and provides a predetermined output. In addition, the controller provides a predetermined output based on flow rate information from the flow rate sensor 2a. Based on the various kinds of outputs of the controller, the manifold valve 8 provided on the drink supply piping 7, the actuator (not shown), various kinds of switch valves, various kinds of pumps or the like are controlled.

Next, a method for sterilizing the filling nozzles 2a or filler 2 described above will be described.

(1) When an operation button on a panel of the controller (not shown) is manipulated, the manifold valve 8 disconnects the drink supply path, the cup 9 is placed on the nozzle mouth of the filling nozzle 2a to connect the drain pipe 20 to the filling nozzle 2a, as shown in the right half of FIG. 1.

(2) The pump 6 is then activated to introduce the water or liquid chemical agent into the annular flow path.

(3) While the water or liquid chemical agent is flowing in the annular flow path, temperature information is transmitted from the temperature sensors 10 and 10b disposed at different positions to the controller at regular time intervals.

The F value is calculated for the positions of the temperature sensors 10 and 10b in the same manner as in the first embodiment.

(4) Flow rate information is transmitted from the flow rate sensor 10a attached to each filling nozzle 2a to the controller at regular time intervals.

A relationship between the flow rate of the hot water or liquid chemical agent passing through each filling nozzle 2a and the effect of sterilization of the filling nozzle 2a can be determined by experiment in advance. Based on the result of the experiment, the controller determines whether or not the smallest one of the flow rates of all the filling nozzles 2a has reached the target value.

(5) The controller monitors the flow rate of the hot water or liquid chemical agent at each filling nozzle 2a based on the flow rate information from the relevant flow rate sensor 10a, monitors the representative temperatures of the hot water or liquid chemical agent upstream and downstream of at least one filling nozzle 2a based on the temperature information from the temperature sensors 10 and 10b, and outputs a signal to complete the sterilization process when the flow rate and the representative temperatures reach the respective target values.

That is, when the minimum value of the F values based on the temperature information from the temperature sensors 10 and 10b reaches the target value, and the minimum value of the flow rates detected by the flow rate sensors 10a reaches the target value, the controller issues a signal to complete the sterilization process in the filler 2.

In response to the signal, the pump 6 is stopped, and the cups 9 are removed from the nozzle mouths of the filling nozzles 2a by the actuator (not shown).

When the flow rate at any of the filling nozzles 2a is lower than a flow rate required for sterilization, the controller may issue an alarm notifying a failure of the sterilization process. Based on the alarm, an operator can perform an adjustment to increase the flow rate of the hot water or the like at the relevant filling nozzle 2a.

While SIP is being performed on the filling nozzles 2a, COP (cleaning out of place), which is a cleaning process, or SOP (sterilizing out of place), which is a sterilization process, is performed on the interior of the chamber 3 including the exterior of the filler 2 and the like by injecting water, a cleaning agent, hot water, a liquid or gaseous sterilizer or the like from the spray nozzles 27 arranged at various positions in the chamber 3.

(6) When sterilization with the liquid chemical agent is to be ended, the pump 6 or the like is stopped after the interior of the filler 2 or the like is rinsed with sterilized washing water. Aseptic air is then supplied into the head tank 11 to keep the whole of the drink supply piping 7 at positive pressure.

(7) After that, the process of filling the bottles b with the drink is started, and the drink prepared in the preparation unit is fed from the drink supply piping 7 into the filler 2 and supplied into the bottle b as a container through the filling nozzle 2a of the filler 2. In the filler 2, the drink flows to the filling nozzles 2a through the upper-stage manifold 26a.

The bottle b filled with the drink is fed out of the filler 2 and then capped and sealed by the capper (not shown).

Third Embodiment

Figure 3:
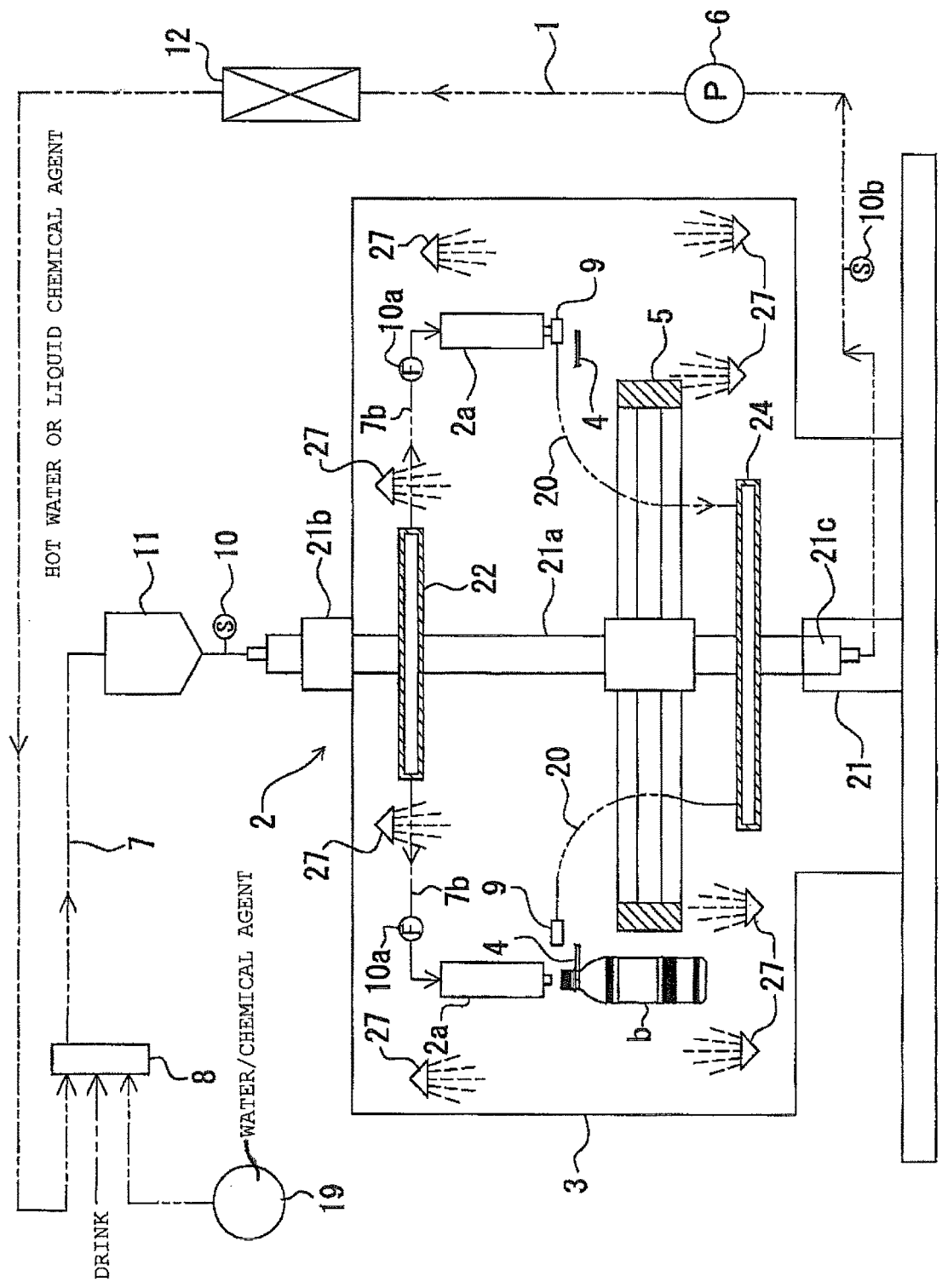
FIG. 3 is a schematic diagram showing a further embodiment of the present invention.

As shown in FIG. 3, according to a third embodiment, an upper rotary joint 21b is provided on an upper part of the pivot 21a. In addition, unlike the first embodiment shown in FIG. 1, a lower rotary joint 21c is provided on a lower part of the pivot 21a.

The lower manifold 24 has a configuration similar to that of the upper manifold 22 and is in communication with the return pipe 1 via the lower rotary joint 21c.

The supply source 19 of the hot water or chemical agent is connected to the drink supply piping 7 via the manifold valve 8.

Next, a method for sterilizing the filling nozzles 2a or filler 2 will be described.

(1) When an operation button on a panel of the controller (not shown) is manipulated, the manifold valve 8 disconnects the drink supply path, the cup 9 is placed on the nozzle mouth of the filling nozzle 2a to connect the drain pipe 20 to the filling nozzle 2a, as shown in the right half of FIG. 3.

(2) The manifold valve 8 opens the flow path from the supply source 19 of the hot water or liquid chemical agent, and the pump 6 is then activated to introduce the hot water or liquid chemical agent into the annular flow path formed by the drink supply piping 7, the drain pipe 20 and the return pipe 1.

Since the pivot 21a is provided with the upper rotary joint 21b and the lower rotary joint 21c at an upper part and a lower part thereof, respectively, the filling nozzles 2a and the like can rotate with the pivot 21a when the hot water or liquid chemical agent is flowing in the annular flow path. Thus, while SIP is being performed on the filling nozzles 2a, COP or SOP is performed on the interior of the chamber 3 including the exterior of the filler 2 and the like by injecting water, a cleaning agent, hot water, a liquid or gaseous sterilizer or the like from the spray nozzles 27 arranged at various positions in the chamber 3. The sterilizer preferably contains liquid or gaseous hydrogen peroxide. However, the sterilizer may contain other constituents, such as acetic acid, peracetic acid, ozone, chlorine dioxide, sodium hypochlorite, sodium hydroxide or potassium hydroxide.

(3) While the hot water or liquid chemical agent is flowing in the annular flow path, temperature information is transmitted from the temperature sensors 10 and 10b disposed at different positions to the controller at regular time intervals.

(4) Flow rate information is transmitted from the flow rate sensor 10a attached to each filling nozzle 2a to the controller at regular time intervals.

A relationship between the flow rate of the hot water or liquid chemical agent passing through each filling nozzle 2a and the effect of sterilization of the filling nozzle 2a can be determined by experiment in advance. Based on the result of the experiment, the controller determines whether or not the smallest one of the flow rates of all the filling nozzles 2a has reached the target value.

(5) The controller monitors the flow rate of the hot water or liquid chemical agent at each filling nozzle 10a based on the flow rate information from each flow rate sensor 2a, monitors the representative temperatures of the hot water or liquid chemical agent upstream and downstream of at least one filling nozzle 10a based on the temperature information from the temperature sensors 10 and 10b, and outputs a signal to complete the sterilization process when the flow rate and the representative temperatures reach the respective target values.

That is, when the minimum value of the F values based on the temperature information from the temperature sensors 10 and 10b reaches the target value, and the minimum value of the flow rates detected by the flow rate sensors 10a reaches the target value, the controller issues a signal to complete the sterilization process in the filler 2.

In response to the signal, the pump 6 is stopped, the pipe line from the supply source 19 of the hot water or liquid chemical agent is disconnected by the manifold valve 8, and the cups 9 are removed from the nozzle mouths of the filling nozzles 2a by the actuator (not shown).

When the flow rate at any of the filling nozzles 2a is lower than a flow rate required for sterilization, the controller may issue an alarm notifying a failure of the sterilization process. Based on the alarm, an operator can perform an adjustment to increase the flow rate of the hot water or the like at the relevant filling nozzle 2a.

While SIP is being performed on the filling nozzles 2a, COP, which is a cleaning process, or SOP, which is a sterilization process, is performed on the interior of the chamber 3 including the exterior of the filler 2 and the like by injecting water, a cleaning agent, hot water, a liquid or gaseous sterilizer or the like from the spray nozzles 27 arranged at various positions in the chamber 3.

(6) When sterilization with the liquid chemical agent is to be ended, the pump 6 or the like is stopped after the interior of the filler 2 or the like is rinsed with sterilized washing water. Aseptic air is then supplied into the head tank 11 to keep the whole of the drink supply piping 7 at positive pressure.

(7) After that, the process of filling the bottles b with the drink is started, and the drink prepared in the preparation unit is fed from the drink supply piping 7 into the filler 2 and supplied into the bottle b as a container through the filling nozzle 2a of the filler 2.

The bottle b filled with the drink is fed out of the filler 2 and then capped and sealed by the capper (not shown).

The present invention is configured as described above. However, the present invention is not limited to the embodiments described above, and various modifications can be made without departing from the spirit of the present invention.

REFERENCE NUMERALS 2 filler
2a filling nozzle
7 drink supply piping
10a flow rate sensor

The invention claimed is:

1. An apparatus for sterilizing a plurality of filling nozzles, comprising:
    a flow rate sensor provided on each of the plurality of filling nozzles, a hot water or liquid chemical agent being fed to drink supply piping that feeds a drink to the plurality of filling nozzles at the same time, a flow rate of the hot water or liquid chemical agent being detected at all the filling nozzles by the respective flow rate sensors while the hot water or liquid chemical agent is being discharged from all the filling nozzles,
    a temperature sensor provided to measure a representative temperature of the hot water or liquid chemical agent downstream of at least one filling nozzle,
    a SIP (Sterilizing in Place) cup connected to a nozzle mouth of each filling nozzle,
    a drain pipe formed by a flexible pipe connected to each SIP cup, the drain pipe being provided with the temperature sensor,
    a return pipe extended from the drain pipe to a manifold valve, the return pipe being provided with a heater, and
    a controller provided with transmitted information about the representative temperature measured by the temperature sensor, the controller configured to calculate an F value based on the representative temperature, and to issue a signal to complete an SIP when both the flow rate at each filling nozzle and the F value calculated based on the representative temperature reach respective target values, the controller comparing the representative temperature measured with a reference temperature and providing a predetermined output, and the hot water or liquid chemical agent being heated to a predetermined temperature by the heater and is circulated in an annular flow path formed by the drink supply piping, the drain pipe and the return pipe,
    wherein the representative temperature of the hot water or liquid chemical agent on the downstream side of the at least one filling nozzle is measured by the temperature sensor provided in the drain pipe at a part outside an aseptic chamber.

2. The apparatus for sterilizing a plurality of filling nozzles according to claim 1, wherein a drink metering sensor provided on each filling nozzle is used as the flow rate sensor.

3. The apparatus for sterilizing a plurality of filling nozzles according to claim 1, wherein an alarm notifying a failure of the SIP is issued if the flow rate at any of the filling nozzles is lower than a flow rate required for sterilization.

4. The apparatus for sterilizing a plurality of filling nozzles according to claim 1, wherein all the filling nozzles are capable of integrally rotating, and during the rotation, an interior and an exterior of the filling nozzles are sterilized at the same time by blasting hot water or a liquid or gaseous chemical agent to the exterior of all the filling nozzles while the hot water or liquid chemical agent is being discharged from all the filling nozzles.

5. The apparatus for sterilizing a plurality of filling nozzles according to claim 4, wherein the interior and the exterior of the filling nozzles are also washed at the same time with the hot water or liquid chemical agent.

6. The apparatus for sterilizing plurality of filling nozzles according to claim 2, wherein an alarm notifying a failure of the SIP is issued if the flow rate at any of the filling nozzles is lower than a flow rate required for sterilization.

* * * * *